(12) United States Patent
Wach et al.

(10) Patent No.: US 8,147,479 B1
(45) Date of Patent: Apr. 3, 2012

(54) MONITORING STRESS ON A THERAPEUTIC AGENT DURING PATIENT DELIVERY

(75) Inventors: Michael L. Wach, Alpharetta, GA (US); W. Robert Taylor, Stone Mountain, GA (US); Raymond P. Vito, NW Atlanta, GA (US); Jack C. Griffis, III, Decatur, GA (US)

(73) Assignee: Cell Precision, LLC, Atlanta, GA (US)

( * ) Notice: Subject to any disclaimer, the term of this patent is extended or adjusted under 35 U.S.C. 154(b) by 0 days.

(21) Appl. No.: 12/460,097

(22) Filed: Jul. 14, 2009

(51) Int. Cl.
*A61M 31/00* (2006.01)
(52) U.S. Cl. .................................................. 604/522
(58) Field of Classification Search ............. 604/522, 604/19, 21, 48, 507, 65
See application file for complete search history.

(56) References Cited

U.S. PATENT DOCUMENTS

2007/0106208 A1* 5/2007 Uber et al. ..................... 604/65
* cited by examiner

*Primary Examiner* — Jackie Ho
*Assistant Examiner* — Deanna K Hall

(57) ABSTRACT

A physician, nurse, or other healthcare practitioner can deliver a therapeutic agent to a patient in a manner that maintains effectiveness of the therapeutic agent, via monitoring and controlling shear, stress, or other potentially detrimental effect. A gauge, meter, or other monitoring device can provide an indication of shear (or other effect) that the therapeutic agent is experiencing during delivery. The monitoring device can provide information relevant to delivering the therapeutic agent in a manner that maintains effectiveness, thereby guiding the practitioner during delivery. For example, the monitoring device can display an estimate of shear based on sensing flow rate or pressure. The therapeutic agent can comprise one or more therapeutic cells, such as progenitor cells or stem cells, or some other healing substance delivered via a cardiac catheter to the patient's cardiovascular tissue, for example.

20 Claims, 8 Drawing Sheets

MONITORING STRESS ON A THERAPEUTIC AGENT DURING PATIENT DELIVERY

FIELD OF THE TECHNOLOGY

The present technology generally relates to delivering therapeutic agents to patients, and more particularly to monitoring a potentially deleterious effect applied to a therapeutic agent during catheter-based delivery. The therapeutic agent can comprise stem cells, progenitor cells, drugs, nanostructures carrying cellular or pharmaceutical payloads, etc. delivered via a catheter to treat diseased or otherwise impaired tissue of a patient's cardiovascular system. For example, a gauge can monitor shear and/or stress experienced by therapeutic cells in the catheter.

BACKGROUND

Certain medical treatments involve inserting a tube, such as a catheter, a needle, a cannula, an endoscope, etc., into a patient and delivering a therapeutic agent to the patient via the tube. In some cases, the tube delivers the therapeutic agent for a systemic impact, for example so the therapeutic agent disperses throughout the patient to treat a disease that is likewise spread throughout the patient's body. In other cases, the tube delivers the therapeutic agent to a specific site that is diseased or that may otherwise need treatment. For example, such a site might be a diseased area of a heart, an artery, or a vein; a lesion; or cardiovascular tissue that is ischemic, necrotic, or otherwise impaired.

However, the effectiveness of certain therapeutic agents may diminish as result of biomechanical force, shear, or stress experienced during delivery. For example, excessive shear, shear force, or stress can impair the ability of a stem cell or a progenitor cell to function as intended, to evolve, to differentiate, to grow properly, or even to live. At an extreme, excessive shear can damage or even rupture cell membranes or cause lysis. More insidiously, lower levels of shear can negatively impact a cell's therapeutic potential, in a manner that may compromise treatment or produce an unexpected result. In the case of relatively new treatments, the amount of stress or shear that a therapeutic agent can tolerate during delivery may not be well known, and success of such treatments can be at risk.

One approach to delivering therapeutic agents that are susceptible to stress-induced damage involves simply extending the time span of delivery, based on the premise that slower delivery will translate to lower stress. However, overly extending delivery time is often undesirable. For example, delivery of stem or progenitor cells to cardiovascular tissue may involve blocking or occluding blood flow during cell delivery, such as via inflating a balloon situated in a vascular lumen. Blocking blood flow for an extended amount of time can have dire consequences, including causing ischemia or even death.

In view of the aforementioned representative deficiencies in the art (or some other related shortcoming), need exists for an improved technology for delivering therapeutic agents that are susceptible to shear, stress, lysis, unintended transformation, undesirable response or mutation, or some other potentially detrimental condition or change associated with delivery. Need also exists for a method and system that can monitor or detect shear, stress, lysis, or some other potentially detrimental condition that a therapeutic agent may experience during delivery. A further need exists for a tool that can provide guidance or feedback to a physician or some other healthcare practitioner during a therapeutic intervention so that the practitioner can avoid inadvertently reducing the effectiveness of the therapeutic agent. Yet another need exits for a technology that can help a healthcare practitioner deliver a therapeutic agent at an appropriate rate. A technology addressing one or more such needs would benefit healthcare via increasing treatment effectiveness and efficiency.

SUMMARY

The present invention can support delivering a therapeutic agent to a patient in a manner that promotes, sustains, or enhances effectiveness of the therapeutic agent.

In one aspect of the present invention, a healthcare practitioner can monitor a level or amount of stress, shear, and/or biomechanical force or effect that the therapeutic agent is experiencing as the therapeutic agent is being delivered to the patient. With this information, the healthcare practitioner can better manage and/or control delivery of the therapeutic agent so that the delivered therapeutic agent retains its intended function, such as a capability for curing, healing, therapy, cell differentiation, tissue restoration or regeneration, treatment, etc.

Monitoring stress on the therapeutic agent can comprise one or more gauges, meters, indicators, instruments, etc. evaluating such stress and providing evaluation results for the healthcare practitioner. The stress can be evaluated in "real time," substantially as the stress occurs, or without a substantial amount of delay that a human would ordinarily perceive or consider substantial annoying, for example. Accordingly, the evaluation can proceed at a pace that provides sufficient time for intervening to bring stress to an acceptable level. Alternatively, the stress can be evaluated and stored (e.g. digitally) for later review. Evaluation results can be presented (for example shown or displayed) on a screen, a display, or a monitor for visual perception; output in the form of a sound (such as a tone, a bell, a voice, a recording, noise, etc.) that the practitioner can hear; provided as vibration, force feedback, or tactilely for reception via touch or feel; or in some other appropriate manner or format that the practitioner can sense (this is not an exhaustive accounting of options for handling evaluation results). Further, the evaluation results can be sent to a non-human recipient, such as a computer, a piece of equipment, storage media, a communications device, or a controller, to name a few representative options out of many other possibilities.

Delivering the therapeutic agent can comprise transporting the therapeutic agent via a tube, a catheter, an endoscope, a cannula, a needle, a syringe, etc.; carrying the therapeutic agent on or in a delivery vehicle; administering the agent through a channel; or moving the therapeutic agent using any appropriate drug- or cell-delivery system.

The term "stress," as used herein, generally refers to a response of a therapeutic agent to a stimulus or influence that can disturb, interfere, or otherwise impact effectiveness or efficacy of the therapeutic agent. Herein, the term's usage further encompasses conditions and effects that can reduce, change, or interfere with normal and/or desired functioning of a cell or an organism, a state of a cell relevant to the cell's treatment capability, or a physiological equilibrium. Examples of stress can include shear; shear force; shear stress; shear rate; strain; pressure; physical interaction between the therapeutic agent (or some component thereof) and a surface of a tube or channel transporting the therapeutic agent; force of acceleration or deceleration; jerk; sudden deceleration; rapid change in pressure; pressure impulses, spikes, or transients; stress associated with rupture; propensity to degrade a cellular structure or membrane; a tendency to induce lysis; some physical, chemical, or biological condition that can result in or contribute to an unwanted change in metabolic activity, curing capability, or effectiveness; a biomechanical force or effect on a therapeutic cell; or some other phenomenon or phenomena potentially impacting the therapeutic agent negatively, in an unwanted manner, or even beneficially; to provide a few representative examples without limitation.

The therapeutic agent can comprise one or more therapeutic cells (such as stem cells, progenitor cells, cells having a capability to differentiate into a specific type of cell, or cells emitting or triggering emission of a healing biochemical after delivery into a patient), a pharmacological liquid or solid, a nano-particle, a drug, a therapeutic compound disposed in a time-release vehicle less than about ten microns in at least one dimension, one or more therapeutic chemicals or cells jacketed in a material (that may be synthetic, biological, or some combination thereof) for delivery, an active payload carried in a nano-scale system or structure (for example less than one or two microns in at least one dimension), nanostructures or other constructs (synthetic, biological, or some combination thereof) carrying pharmaceutical or cellular payloads, etc. (this is not an exhaustive or limiting list of types of therapeutic agents).

The discussion of delivering therapeutic agents presented in this summary is for illustrative purposes only. Various aspects of the present invention may be more clearly understood and appreciated from a review of the following detailed description of the disclosed embodiments and by reference to the drawings and the claims that follow. Moreover, other aspects, systems, methods, features, advantages, and objects of the present invention will become apparent to one with skill in the art upon examination of the following detailed description and the figures. It is intended that all such aspects, systems, methods, features, advantages, and objects are to be included within this description, are to be within the scope of the present invention, and are to be protected by the accompanying claims.

BRIEF DESCRIPTION OF THE DRAWINGS

FIG. 8, are a flowchart of a process for delivering a therapeutic agent while monitoring stress on the therapeutic agent in accordance with certain exemplary embodiments of the present invention.

Figure 1A:
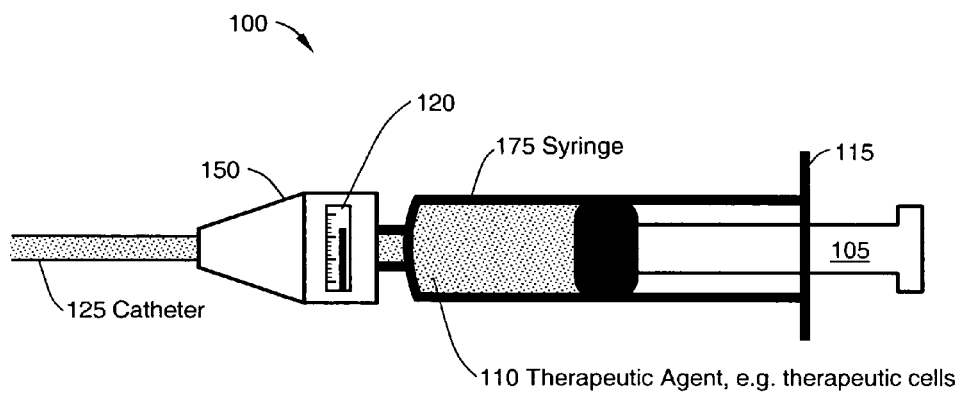
FIG. 1A is an illustration of a system for delivering a therapeutic agent comprising an apparatus for monitoring stress in accordance with certain exemplary embodiments of the present invention.

Many aspects of the present invention can be better understood with reference to the above drawings. The elements and features shown in the drawings are not necessarily to scale, emphasis instead being placed upon clearly illustrating principles of exemplary embodiments of the present invention. Moreover, certain dimensions may be exaggerated to help visually convey such principles. In the drawings, like reference numerals designate like or corresponding, but not necessarily identical, elements throughout the several views.

DETAILED DESCRIPTION OF EXEMPLARY EMBODIMENTS

An exemplary embodiment of the present invention can facilitate monitoring delivery of a therapeutic agent so the delivered therapeutic agent retains its effectiveness.

Delivery of a therapeutic agent can be viewed as a mechanical event characterized by exertion of forces, stresses, and strains on the therapeutic agent during delivery. With the therapeutic agent comprising a biological component, such as living cells, the event can be a biomechanical event. As a consequence of such forces, stresses, and strains, the biomechanical event can result in cell death, altered cell function, therapeutic agent degradation, etc. Monitoring exertions of forces, stresses, and/or strains of the biomechanical event can provide beneficial information, for example helping minimize, control, optimize, understand, model, and/or ameliorate the biomechanical effects. In particular, such monitoring can help avoid adverse biomechanical effects that can negatively influence the desired function of the therapeutic agent.

Figure 7:
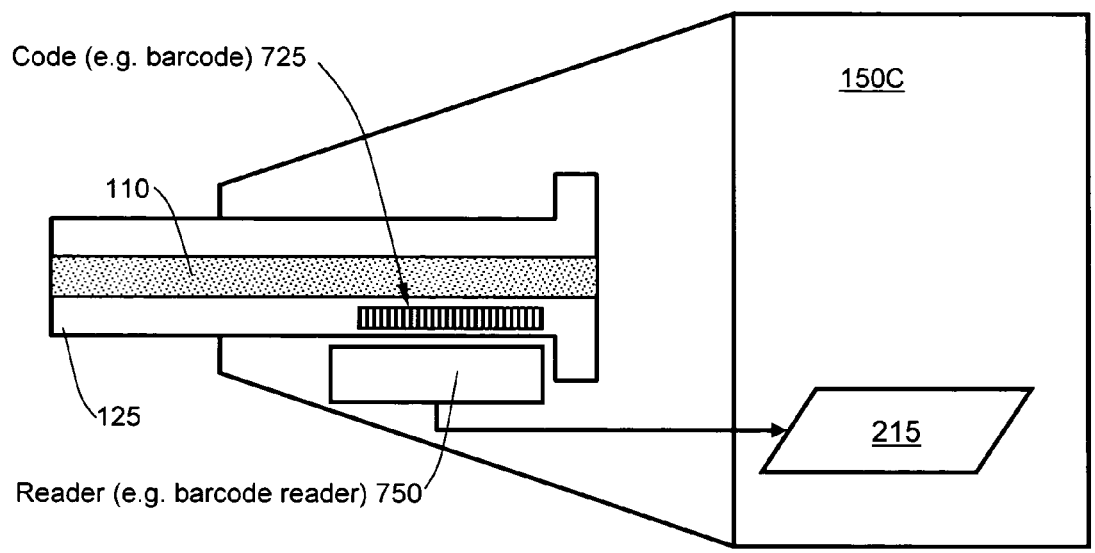
FIG. 7 is a schematic of an apparatus that reads information from a component of a therapeutic agent delivery system in support of monitoring stress experienced by a therapeutic agent in accordance with certain exemplary embodiments of the present invention.
Figure 8A:
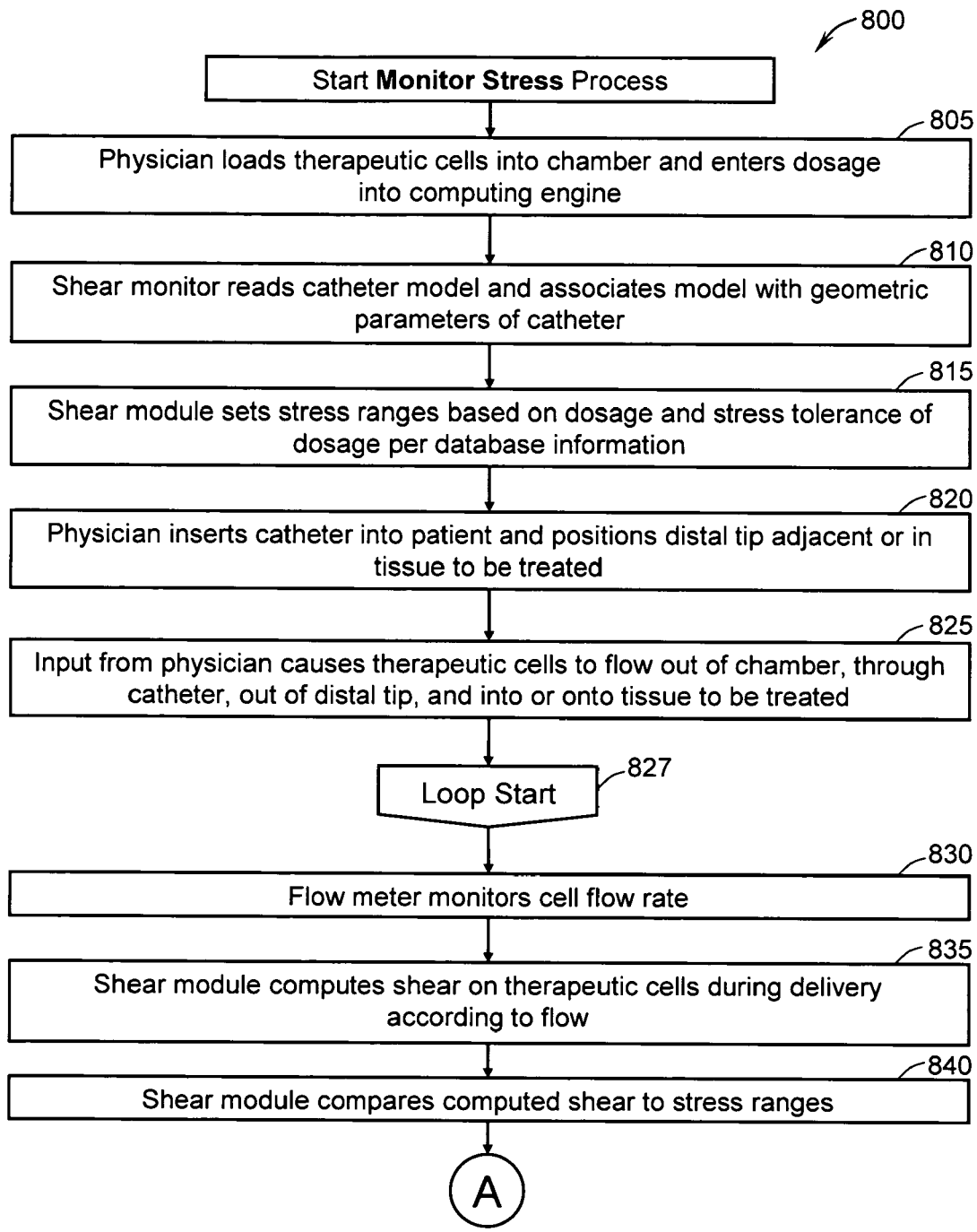
FIGS. 8A and 8B, collectively

Technology for monitoring therapeutic agent delivery will be described more fully hereinafter with reference to FIGS. 1-8, which depict representative or illustrative embodiments of the present invention. FIGS. 1A and 2-7 illustrate examples of therapeutic agent delivery systems that comprise a capability for monitoring at least some delivery parameter relevant to effectiveness of the delivered therapeutic agent. FIG. 1B illustrates a representative operating environment, while FIG. 8 illustrates a representative method or process comprising monitoring delivery of a therapeutic agent.

The present invention can be embodied in many different forms and should not be construed as limited to the embodiments set forth herein; rather, these embodiments are provided so that this disclosure will be thorough and complete, and will fully convey the scope of the present invention to those having ordinary skill in the art. Furthermore, all "examples" or "exemplary embodiments" given herein are intended to be non-limiting, and among others supported by representations of the present invention.

Figure 1B:
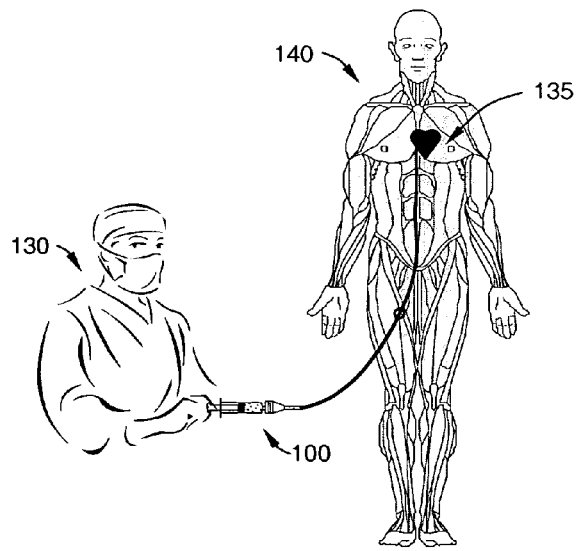
FIG. 1B is an illustration of operating a system for delivering a therapeutic agent comprising an apparatus for monitoring stress in accordance with certain exemplary embodiments of the present invention.

Turning now to FIGS. 1A and 1B (collectively FIG. 1), FIG. 1A illustrates an exemplary system 100 for delivering a therapeutic agent 110 comprising an apparatus 150 for monitoring stress according to certain embodiments of the present invention. Meanwhile, FIG. 1B illustrates operating an exemplary system 100 for delivering a therapeutic agent 110 comprising an apparatus 150 for monitoring stress according to certain embodiments of the present invention. Thus, FIG. 1B illustrates a typical application of the system 100 that FIG. 1A illustrates.

In an exemplary embodiment, the apparatus 150 for monitoring stress monitors at least one delivery condition or parameter relevant to maintaining effectiveness of the therapeutic agent. The apparatus 150 for monitoring stress typically monitors, detects, evaluates, senses, or determines a parameter associated with the therapeutic agent 110 that delivery may impact, change, vary, or modulate based on how the delivery proceeds. In an exemplary embodiment, the apparatus 150 for monitoring stress can comprise a shear monitor and thus will be referred to as the shear monitor 150. As discussed herein, shear is one representative example of monitoring stress that may be imposed on a therapeutic agent 110 during delivery. Accordingly, the shear monitor 150 provides an exemplary embodiment of a stress monitor. Further, in the exemplary context of avoiding cell lysis, the shear monitor 150 can be viewed as a "lysometer."

The term "shear," as used herein, generally refers to: a force, movement, or pressure applied to a body perpendicular to a given axis, with greater force on one side of the axis than on the other side; lateral deformation produced in a body by an external force; a load, force, or system of forces producing a strain; the action on a body by a system of balanced forces whereby strain or deformation results; the internal resistance or reaction of a generally elastic body to external forces applied to the body; a stress applied parallel or tangential to a surface of a body; force acting on a fluid in a direction perpendicular to an extension of the fluid, like the pressure of air along the front of an airplane wing; or a strain that acts parallel to a face of a material upon which the strain acts. The term "shear," as used herein, generally encompasses shear force; shearing force; shear strain; shearing strain; shearing stress; shear stress; fluid shear stress; engineering shear strain; and average shear strain.

Those skilled in the art having benefit of this disclosure will appreciate that a viscous fluid (including air and water) moving along a solid boundary will incur shear adjacent the boundary. While the speed of the fluid at the boundary may approach zero, at some height from the boundary, the flow speed substantially equals that of the fluid. The region between these two locations can be referred to as the boundary layer. Shear stress can result from such a change in velocity.

In an exemplary embodiment, the therapeutic agent 110 can comprise progenitor cells or stem cells in an aqueous medium, a carrier fluid, or some other viscous or relatively non-viscous fluid, and thus will be referred as the therapeutic cells 110 in the context of a representative example. As discussed above, in various exemplary embodiments, the system 100 can deliver a wide range of therapeutic agents in connection with treating various diseases or maladies. Examples of therapeutic agents include vectors; living cells; viruses having therapeutic potential; drugs; pharmaceutical agents; one or more pharmacologically active ingredients disposed in a delivery vehicle, a shell, or a casing; drug carrier systems; capsules containing drugs; biochemicals susceptible to various delivery conditions or forms of delivery stress; functionalized molecules; proteins; carbohydrate compounds and materials; small molecules compounds that may be sensitive to some aspect of delivery; and masses of cells that have begun to form into a tissue structure, without being exhaustive.

A syringe 175 holds the therapeutic cells 110 in preparation for delivery and during delivery. Thus, the illustrated syringe 175 provides an exemplary embodiment of a chamber in which the therapeutic cells 110 reside during at least some portion of delivery. The term "chamber," as used herein, generally refers to a space, region, volume, or area that is substantially enclosed (though not necessarily entirely enclosed). Thus, usage of the term "chamber" is intended to be consistent with an ordinary meaning, rather than being a term of art with some special meaning unique to delivery technologies. A chamber may include an inlet, an outlet, input and output ports, and open areas while remaining substantially enclosed, for example. Tanks, vessels, storage facilities, pumps, catheters, tubes, containers, housings, needles, syringes, endoscopes, cannulas, and various other systems typically comprise chambers (and the therapeutic cells 110 can be disposed in chambers of such devices).

When the physician 130 applies compressive force between the lip 115 and the plunger 105 of the syringe 175, the plunger 105 depresses, thus pressurizing the therapeutic cells 110. In response to the applied pressure, the therapeutic cells 110 exit the syringe 175 and flow through the shear monitor 150 and into the catheter 125. The catheter 125 delivers the therapeutic cells 110 to the cardiovascular or other system 135 of the patient 140. As will be appreciated by one of ordinary skill in the art having benefit of this disclosure, a cardiovascular system comprises arteries, veins, a heart, and supporting tissues. Thus, the patient's cardiovascular system and cardiovascular tissues include the system that circulates blood within the patient 140.

In certain exemplary embodiments, the catheter 125 includes one or more distal needles for delivering the therapeutic cells 110 into or through a vascular lumen, such as an artery, a vein, or certain structures of the heart. Thus, the catheter 125 can comprise various types of end effectors and distal tips for manipulating tissue, piercing tissue, and/or delivering therapeutic cells into tissue. In certain exemplary embodiments, the catheter 125 delivers the therapeutic cells 110 into the patient's blood stream, for example adjacent or immediately upstream from a site needing therapy. Such a site can comprise tissue damaged or placed at risk by a heart attack or an ischemic event, for example.

Moreover, in certain exemplary embodiments, the catheter can be replaced by another tube or facility that can deliver a therapeutic agent to some organ or portion of an organism, be it the patient 140, a non-human mammal, or a laboratory subject, for example. Other examples of delivery sites can include wounds, the renal system, the bladder, portions of the eye, the pancreas, lungs, esophagus, skin, reproductive organs, etc. In certain exemplary embodiments, the shear monitor 150 monitors stress associated with delivering the therapeutic cells 110 to ex vivo tissue, for example in the context of growing organs in a laboratory for ultimate attachment to a person.

The shear monitor 150 senses or detects one or more parameters of the therapeutic cells 110 moving between the syringe 175 and the catheter 125. In various exemplary embodiments, other monitors, sensors, and detectors can be substituted for the shear monitor 150. Accordingly, the shear monitor 150 provides an example of a system that more generally can monitor either a biomechanical event (for example, shear stress, pressure, fluctuating pressure, shear rate, etc) or the effects of the biomechanical event (for example, cell expression of various substances, such as lactate, protein, etc.; cell death; cell injury; degradation of pharmaceutical agent; etc.).

As will be discussed in further detail below, an exemplary embodiment of the shear monitor 150 senses or detects flow rate of the therapeutic cells 110, computes or estimates shear based on the flow rate and certain geometrical attributes of the catheter 125 and the system 100, and outputs an indication of shear or stress for observation or review by the physician 130. The shear monitor 150 comprises a stress indicator 120 that shows the indication of shear or stress in a format conducive to reception by the physician 130. The physician 130 typically uses information from the stress indicator 120 as feedback or guidance for cell delivery. In certain exemplary embodiments, stress or shear is presented in a range format, for example as a color-coded index of risk. For example, the physician 130 can reduce the force applied to the plunger 105 of the syringe 175 if the stress indicator 120 indicates that the shear applied to the therapeutic cells 110 is approaching a level that may detrimentally impact cell effectiveness. Thus, the physician 130 can adjust the rate of plunger depression to maintain stress within an acceptable limit during cell delivery.

Figure 2:
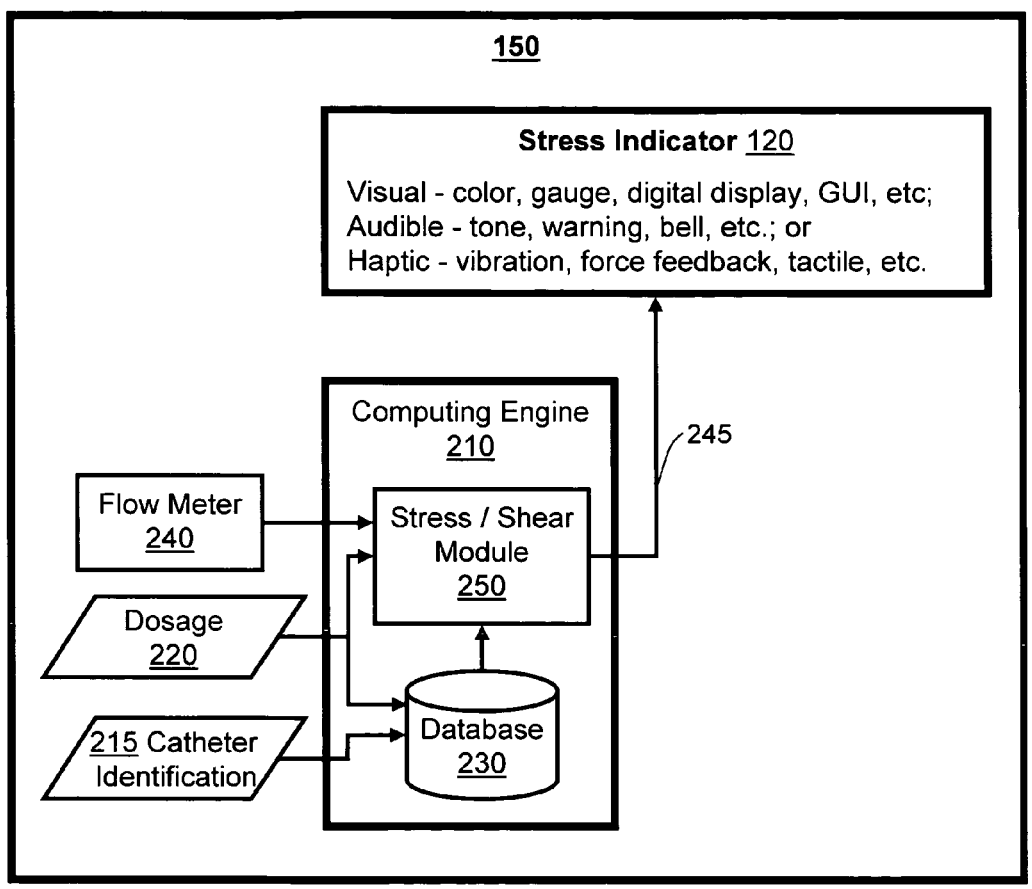
FIG. 2 is a functional block diagram of a system for monitoring stress applied to a therapeutic agent in connection with delivery of the therapeutic agent in accordance with certain exemplary embodiments of the present invention.

Turning now to FIG. 2, this figure illustrates an exemplary functional block diagram of a system 150 for monitoring stress applied to a therapeutic agent 110 in connection with delivery of the therapeutic agent 110 according to certain embodiments of the present invention. Moreover, FIG. 2 illustrates an exemplary embodiment of the shear monitor 150 illustrated in FIG. 1 and discussed above and thus will be discussed below in that context.

The shear monitor 150 comprises a flow meter 240 that senses or detects flow rate of the therapeutic cells 110 flowing into the catheter 125 and thus typically through the catheter 125. In certain exemplary embodiments, the flow meter 240 comprises at least two pressure sensors that measure pressures at two locations in the flow path of the therapeutic cells 110. In certain exemplary embodiment, the pressure sensors are fiber optic sensors that provide an optical output, such as available from Fiso Technologies, Inc. of Quebec, Canada under the product identifiers FOP-F125, FOP-M, FOP-MIV, or FOP-MS. In certain exemplary embodiments, the pressure sensors emit electrical signals, such as the Model 060 or the Model 060S pressure sensors available from Precision Measurement Company of Ann Arbor, Mich. For example, the two pressure sensors or pressure detectors can be respectively located in two locations of the flow path having different cross sectional dimensions. One sensor can be located in the main portion of the syringe 175 holding the therapeutic cells 110, while the other sensor can be located at an entrance of the catheter 125 or in the connection between the catheter 125 and the syringe 175. Alternatively, two pressure sensors can be positioned in a neck of a fitting (e.g. a luer fitting) so the internal diameter changes between the two sensors. As will be appreciated by one of ordinary skill having the benefit of this disclosure, the pressure differential between the two locations correlates with flow rate, typically in accordance with the Bernoulli equation (or a first-order approximation thereof). Accordingly, the two pressure signals respectively output by the two detectors provide a flow rate measurement. That is, two pressure sensors or detectors can provide an exemplary embodiment of the flow meter 240, specifically a differential pressure flow meter.

The term "sensor," as used herein, generally refers to a device, system, or apparatus that senses. The term "detector," as used herein, generally refers to a device, system, or apparatus that detects. The term "transducer," as used herein, generally refers to a device, system, or apparatus that provides a signal comprising one form of energy in response to receiving a signal comprising another form of energy.

In an alternative exemplary embodiment, the flow meter 240 comprises an ultrasonic flow meter, for example either a transit time ultrasonic flow meter or a Doppler shift ultrasonic flow meter, that detects flow without necessarily contacting the therapeutic cells 110. In another exemplary embodiment, the flow meter 240 comprises an electromagnetic flow meter. In yet another exemplary embodiment, the flow meter 240 comprises a Doppler shift flow meter utilizing a technology other than ultrasound. In still another exemplary embodiment, the flow meter 240 comprises a laser sensor that measures flow via illuminating the therapeutic cells 110 with laser light and analyzing the laser light returning from the flowing therapeutic cells 110. In another exemplary embodiment, the flow meter 240 comprises an optical time-of-flight flow meter.

In one exemplary embodiment, the flow meter 240 is a laser Doppler flow meter such as the Model Number ML191 laser Doppler Flow Meter, available from ADInstruments Pty Ltd. of Colorado Springs, Colo. ADInstruments provides a variety of suitable probe options for that flow meter suited for monitoring therapeutic agents in accordance with the disclosed teaching, including "fine needle probe" Model Number MNP110XP and "pencil probe" Model Number MNP100XP.

In one exemplary embodiment, the flow meter 240 comprises the ultrasonic flow system of ADInstruments that is marketed under the product identifier "ML870B12." The flow meter 240 can also comprise an ultrasonic tubing flow sensor of Transonic Systems, Inc. of Ithaca N.Y. that operates under the principle of ultrasonic transit time. The Transconic product marketed under the product identifier "ME-PXL-Series" is compatible with the instruments of ADInstruments and is available from ADInstruments. Further, Transconic offers a line of ultrasonic tubing sensors that clamp on flexible tubing for non-contact flow measurement of fluids flowing through the tubing. Thus, the catheter 125 (or a tube connected thereto) can feed through a flow sensing device that measures the flow rate of the therapeutic cells 110 moving through the catheter 125. Accordingly, the flow meter 240 can comprise at least one ultrasonic transducer. In some exemplary embodiments, the flow meter 240 comprises two transducers, one for emitting ultrasonic signals based on electrical signals, and one for receiving ultrasonic signals and converting those received signals into electrical signals.

In one exemplary embodiment, the flow meter 240 comprises a magnetic flow meter, such as one available from ABB of Warminster, Pa., including the products that company markets under the product identifiers "FXE4000" and "FXM2000." Accordingly, the flow meter 240 can comprise a magnetic transducer or electromagnetic transducer.

In certain exemplary embodiment, the flow meter 240 incorporates exactly one pressure detector or sensor. Accordingly, the flow meter 240 can infer flow from a pressure measurement based on information about the geometry (e.g. internal dimensions) of the catheter 125 and assumptions about the pressure at the distal outlet of the catheter 125. For example, the pressure at the outlet of the catheter 125 can be estimated based on knowledge of the human cardiac system.

In certain exemplary embodiments, a pressure sensor or detector can take the place of the flow meter 240 (or augment the flow meter 240). Such a pressure sensor can detect rapid changes in pressure that may damage the therapeutic cells 110 or otherwise impact their effectiveness in an unintended manner, for example. That is, certain therapeutic agents can be susceptible to change in pressure (or pressure transients or impulses), and the shear monitor 150 can monitor pressure change and factor change in pressure into the stress indications output by the stress indicator 120. Thus, the physician 130 can receive information about stress based on pressure experienced by the therapeutic cells 110 as a function of time or pressure gradient.

In applications in which the catheter 125 is injecting the therapeutic cells 110 into muscular tissue or the myocardium of the patient's pulsing heart, cell shear may change significantly during each beating cycle of the heart. The therapeutic cells 110 may experience a peak in the level of shear, for example in connection with the heart muscle contracting and relaxing as it beats. In other words, heart beats may produce pressure transients or flow transients that result in stress and/or shear transients. Accordingly, the flow meter 240 can provide an appropriate speed of response for detecting abrupt changes in flow.

In certain exemplary embodiments, the shear monitor 150 correlates flow or pressure measurements with a selected portion of the cardiac cycle. An instrument (not illustrated) acquires an electrocardiogram ("EKG") or an EKG signal from the patient 140 that is received by the computing engine 210. The EKG/EKG signal informs the computing engine 210 about the flow (and/or pressure) detected at each stage or point of the patient's heart-beat cycle. Thus, the computing engine 210 can select flow and/or pressure measurements acquired at time(s) of interest within the heart cycle. For example, the flow or pressure taken when the heart is in a relaxed state (or alternatively in some other state) may be more relevant to shear or stress, and the shear monitor 150 (and/or the stress indicator 120) can preferentially use those measurements. Moreover, for each patient 140 flow and pressure measurements can be acquired and archived with the corresponding EKG so that this information can be used in the future. In this manner, the database 230 can be refined over time as information is acquired about shear conditions that led to successful therapies (and the shear conditions associated with undesirable therapeutic outcomes).

Whether or not an EKG signal is acquired, the computing engine 210 receives the flow measurement (typically but not necessarily as an electrical signal) from the flow meter 240 along with a dosage 220 and a catheter identification 215. The dosage 220 specifies the amount of the therapeutic cells 110, typically as input by the physician 130. The catheter identification 215 identifies the specific type of the catheter 125, for example including a manufacturer and model number. In one exemplary embodiment, the physician 130 inputs the catheter identification 215 and/or the dosage 220, for example via a keypad. As discussed below, FIG. 7 illustrates another exemplary embodiment in which the catheter identification 215 is automatically read from the catheter 125.

The computing engine 210 includes a database 230 containing physical dimensions, parameters, and/or other information about various catheters 125 that the physician 130 may select. The computing engine 210 retrieves from the database 230 the dimensions, parameters, and information according to the catheter identification 215. Such dimensions, parameters, and information can include catheter length, internal dimensions of the catheter 125, needle dimensions as appropriate for catheters 125 comprising one or more distal needles, properties of the materials lining the catheter 125 and interacting with the therapeutic cells 110 (typically via contact), etc. The database 230 can be local, within a common housing of the computing engine, linked via a local area network ("LAN"), or remotely assessable via communication (wireless or wired) from a remote server or storage facility (e.g. via the Internet or a wide area network ("WAN").

As discussed in further detail below, the database 230 can further contain information about various types of therapeutic cells 110 that the physician 130 may select for administering.

For example, the database 230 can contain a lookup table that associates stress and/or shear tolerances to a wide range of therapeutic agents. Accordingly, the shear module 250 can determine shear tolerance according to dosage information entered by the physician 130.

In certain exemplary embodiments, the computing engine 210 comprises a microcontroller, a microprocessor, and/or other digital circuitry that may include flash memory, random access memory ("RAM"), timers, one or more analog-to-digital converters ("ADCs"), and/or one or more digital-to-analog converters ("DACs"). More generally, the computing engine 210 can comprise a central processing unit ("CPU"). Flash memory can facilitate adding or changing software functionality, for example remotely via a link to a wide area network ("WAN"). The computing engine 210 can use such RAM for data storage and program execution. An ADC can digitize analog signals incoming from the flow meter 240 or other sources. The ADC conversion rate or sampling rate can be sufficiently high so as to discriminate shear peaks or transients that may appear, for example during one or more phases of each heart-beat cycle. In certain exemplary embodiments, the ADC conversion rate/time resolution can be at least 1 kilohertz ("KHz"), 2 KHz, 5 KHz, 10 KHz, or 25 KHz, or in a range between any two of those KHz values. In certain exemplary embodiments, the sampling rate is greater than about 100 KHz or about 250 KHz. A DAC can generate analog versions of digitally composed signals, such as for actuating a valve or other apparatus (see FIG. 6, discussed below). Timers can coordinate software execution, measure time between signals or events, or facilitate digital processing activities. One type of timer that the computing engine 210 can comprise is a program interval timer ("PIT") that sends an interrupt to a processor upon counting down to zero from a preset value.

In certain exemplary embodiments, the computing engine 210 comprises erasable programmable read only memory ("EPROM"), which may be electrical erasable programmable read only memory ("EEPROM"), to facilitate upgrading or changing software, database parameters, or calibration data.

The computing engine 210 can further comprise various types of memory such as any one or combination of volatile memory elements (e.g., forms of RAM such as DRAM, SRAM, SDRAM, etc.) and nonvolatile memory elements (e.g., read only memory ("ROM"), hard drive, tape, CDROM, etc.). Further, the computing engine's memory may incorporate electronic, magnetic, optical, and/or other types of storage media and can have a distributed architecture, where various components are situated remote from one another, but can be accessed by a microprocessor or other computer or computing element thereof via one or more communication links or over a communications network.

A "computer-readable medium" can be any means that can store, communicate, propagate, or transport a program or data for use by or in connection with an instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a RAM (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which a program is printed, as the program can be electronically captured, via for instance optically scanning the paper or other medium, then compiled, interpreted or otherwise processed in a suitable manner if necessary, and then stored in a computer memory.

The computing engine 210 can also include logic implemented in hardware with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

In certain exemplary embodiments, the computing engine 210 is implemented in a laptop computer, a handheld computer (see FIG. 3, discussed below), a handheld, a data organizer, a laboratory information management system ("LIMS"), a network computer, a distributing computing system, or a personal computing device. Alternatively, the computing engine 210 can be implemented as an "embedded system," an embedded controller, or a special purpose computer. Thus, the computing engine 210 can include a computing system optimized for monitoring stress of therapeutic agent delivery as described herein. Further, the computing engine 210 can be dedicated to this application rather than supporting a wide range of computing activities. In such an embodiment, the computing engine 210 can be either board mounted or miniaturized.

In certain exemplary embodiments, the computing engine 210 is implemented as a microcontroller or a microcontroller system. Such a microcontroller typically is a computer-on-a-chip, comprising a processor, memory, and input/output functions. The microcontroller can comprise a microprocessor with a high level of integration, in contrast to the general-purpose microprocessors typically found in personal computers. Beyond basic arithmetic and logic elements, the microcontroller integrates read-write memory for data storage, ROM for program storage, EEPROM for permanent data storage, peripheral devices, and input/output interfaces. The microcontroller can be configured to consume a low level of power so that the shear monitor 150 is battery powered. As discussed above, the microcontroller can comprise a PIT. Further, the microcontroller can comprise a time processing unit ("TPU") that can detect input events, generate output events, and handle other useful operations.

The present disclosure and teaching enables one of ordinary skill in the art having the benefit of that disclosure and teaching to implement the computing engine 210 as a microcontroller or microcontroller system without undue experimentation, as microcontroller technology is widely available, well understood, and readily modeled. Microcontrollers are frequently incorporated in a wide range of products and devices, such as automobile engine control systems, computer system peripherals, remote controls, cell phones, watches, calculators, office machines, appliances, microwave ovens, washing machines, power tools, digital thermostats, instruments, and toys.

In an exemplary embodiment, the microcontroller is a unitary or single integrated circuit ("IC") that may comprise: a CPU (e.g. ranging from 4, 8, 16, 32, or 62 bits); discrete input and output bits that support control or detection of a logic state of an external device or line; serial input/output such as one or more universal asynchronous receiver/transmitter ("UART") ports or other communication interfaces such as "I²C," "serial peripheral interface," and "controller area network" for system interconnect; peripherals such as timers, event counters, PWM generators, and watchdog timers; volatile memory (RAM) for data storage; ROM, EPROM, EEPROM, or Flash memory for program and operating parameter storage; a clock generator, in the form of an oscillator, a quartz timing crystal, a resonator, or a resistor-capacitor timing circuit; and an ADC (not an exhaustive list and various embodiments will not include all of these elements).

The computing engine 210 can be a microcontroller in the form of a system-on-a-chip or system on chip ("SoC" or "SOC") wherein the computing engine 210 is integrated in a single IC chip. As such, the SOC may contain digital, analog, and mixed-signal functionality on one chip.

Alternatively, the computing engine 210 can be constructed as a system in package ("SiP") wherein multiple chips are housed in a single package or as a multi-chip module ("MCM"). Further, the computing engine 210 can comprise one or more application specific integrated circuits ("ASICs") or digital signal processing ("DSP") circuits.

Suitable controllers and microcontrollers for various embodiments of the computing engine 210 are available from a wide range of commercial sources, such as: A-WIT Technologies, Inc. of Williamstown, N.J. under the trade identifier "C STAMP;" Comfile Technology Inc. of Foster City, Calif. under the trade identifiers "CUBLOC" and "CuTOUCH" using the Atmel ATmega128 processor; Coridium Corporation of Tahoe Vista, Calif.) under the "ARMexpress" trade identifier; and Elba Corporation of Beaverton Oreg. under the trade identifiers "ZBasic" and "ZX-series," for example.

With the integration and miniaturization technology described in detail above, the computing engine 210 can be attached to the system 100 in the format illustrated in FIG. 1A and discussed above. In certain exemplary embodiments, the shear monitor 150 is smaller than the syringe 175 in at least one dimension. In certain exemplary embodiments, the total volume of space occupied by the shear monitor 150 is less than the total volume of space occupied by the syringe 175. Thus, the shear monitor 150, including the computing engine 210, can be located in a fitting between the catheter 125 and the syringe 175, attached to the catheter 125, and/or attached to the syringe 175. Accordingly, the physician 130 can hold the syringe 175 and the shear monitor 150 as an integrated, handheld unit, with the shear monitor 150 being battery powered, for example. The physician 130 can conveniently view stress or shear information provided by the shear monitor 150 as the physician 130 is dispensing the therapeutic cells 110 via depressing the plunger 105. In this manner, the physician 130 can readily vary the pressure on the plunger 105 to maintain stress within acceptable limits or ranges.

The shear module 250 of the computing engine 210 typically comprises computer executed instructions and/or software routines for computing or estimating shear and/or stress on the therapeutic cells 110 (or another parameter of interest) based on flow information from the flow meter 240, the cell dosage 220, and the physical parameters of the catheter 125, as discussed above. In certain exemplary embodiments, the shear module 250 comprises a computer-based model of the catheter 125 that estimates shear on the therapeutic cells 110 based on flow rate as provided by the flow meter 240, dosage 220, and input from the database 230 regarding physical dimensions of the system 100 that are relevant to shear.

Calculating stress or shear stress to which cells may be exposed in a delivery system, specifically the catheter 125, is typically accomplished using a suitable model of the flow. An example of an appropriate model is the Poiseulle model which relates shear stress, specifically maximum shear stress T, to pressure drop experienced by the flowing material (in this case the therapeutic cells 110, including an associated carrier fluid):

$$\tau = \frac{\Delta P d}{4L}$$

Here, ΔP is the pressure change over length L, and d is the internal diameter of the catheter.

In an exemplary embodiment, shear is computed based on the portion of the catheter 125 having the smallest internal diameter. That is, shear is determined at the longitudinal section of the catheter 125 having the tightest flow restriction. For example, shear may computed at the distal tip of the catheter 125, such as in a needle near where the therapeutic cells 110 exit the catheter 125.

In certain exemplary embodiments, the catheter 125 is mathematically segmented. Shear is computed based on the Poiseulle model or some other appropriate model known in the art for each catheter segment. Total shear and/or total stress is then estimated via integrating the shear or stress from each such catheter segment.

While the Poiseulle equation is one model for analyzing shear due to flow in the catheter 125 other models familiar to those with ordinary skill in the art of fluid mechanics may be similarly employed to calculate shear. The Poiseulle model assumes full developed steady viscous flow of a Newtonian fluid in a rigid circular cylindrical tube. In an alternative approach, the assumption of a Newtonian fluid (i.e. linear viscous fluid) is dropped to include viscous behavior such as nonlinear fluids or fluids exhibiting a finite yield stress.

If flow rate is sufficiently large, turbulence can be a factor worthy of modeling. In this case, friction can be measured experimentally with known laboratory testing readily understood and implemented by one of ordinary skill in the art having the benefit of the present disclosure. From such experimental data, a "friction factor" can be determined from "pipe flow" and published pipe flow tables.

Shear can further be determined via the methodology of "Wormsley flow," which involves fully developed laminar pulsatile flow of a Newtonian fluid in a cylindrical tube having a circular cross section. Further, the effects of wall deformation and non-steady effects (such as turbulence) can be considered in shear/stress computations. Dependence of viscosity of a carrier medium on cell volume fraction can be determined from experimental data in conjunction with a viscosity-shear rate model such as the "Bingham fluid" model. Entrance effects, such as the flow near a tube entrance or an abrupt change in internal diameter can be included in the computations. Numerical solutions of the Navier Stokes equations can be used to numerically solve for shear stress given various assumptions and/or operating constraints.

Accordingly, various models of fluid flow may be used to evaluate biomechanical forces such as shear and shear stress experienced by the therapeutic cells 110 moving through the catheter 125. Such models include, but are not limited to variations of Poiseulle flow, Wormsley flow, consideration of turbulence, and/or numerical solutions of the Navier Stokes equations.

The shear module 250 compares the computed shear to the sensitivity or tolerance of the therapeutic cells 110 to shear. In an exemplary embodiment, the computing engine 210 stores acceptable limits and/or ranges of shear for the therapeutic cells 110, for example in the database 230 or in other local or remote storage. The dosage 220 specifies the type of the therapeutic cells 110, and the computing engine 210 retrieves shear criterion or criteria (e.g. limits) from the database 230.

The shear module 250 evaluates whether the shear being applied to the therapeutic cells 110 is within one or more thresholds. Based on this evaluation, the computing engine 210 sends a shear signal to the stress indicator 120.

As discussed above, shear, such fluid shear stress, can modulate cell function over a large range that is dependent upon the cell type to be used and the intended purpose of the cells. Thus, limiting parameters can be developed for each specific application and therapeutic agent (e.g. type of therapeutic cells 110) to be delivered. The effects of shear magnitude, directionality, integrated magnitude, transients, and other descriptors of shear, forces, and/or biomechanical effects on the therapeutic cells 110 can be assayed using a variety of techniques that can be implemented without undue experimentation by those of ordinary skill in the art having benefit of this disclosure. Such techniques include, but are not limited to, complementary deoxyribonucleic acid ("cDNA") microarray assays, proteomics analyses, western analyses, "polymerase chain reaction" ("PCR") arrays, assays of cell viability, etc. Through the use of one or more of such assays, shear parameters permitting safe and effective delivery of therapeutic agents can be determined. In some instances, it may be beneficial to assure a certain level of shear in order precondition the therapeutic agent for optimal efficacy. Thus, these experimental approaches may define both the upper and lower limits for each of the descriptors of shear stress. Accordingly, appropriate thresholds, criteria, and rules for levels of shear can be determined via laboratory testing conducted on the therapeutic cells 110.

In certain exemplary embodiments, the shear monitor 150 comprises, practices, and/or implements any of the technologies, apparatuses, devices, components, systems, elements, features, methods, processes, or steps disclosed or taught in U.S. patent application Ser. No. 12/454,396, filed on May 18, 2009 with the same inventor list as the present application and assigned to the same entity and entitled "Method and System for Mitigating Effects of Biomechanical Forces on Cell, Particle and Drug Based Therapies," the entire contents of which are hereby incorporated herein by reference. For example, the computing engine 210 can utilize teaching of U.S. patent application Ser. No. 12/454,396 to preferentially select or optimize one or more parameters or conditions associated with therapeutic agent delivery to avoid unintentionally changing efficacy as a result of biomechanical forces or shear incurred during delivery and/or to maintain one or more delivery parameters within a desired range. Further, the shear monitor 150 or the computing engine 210 can practice disclosure of U.S. patent application Ser. No. 12/454,396 in connection with or in support of making one or more decisions or determinations or taking an action as described therein or herein. One of ordinary skill in the art having benefit of this disclosure will be able to apply technologies of U.S. patent application Ser. No. 12/454,396 to the devices, systems, elements, methods, processes, and steps disclosed herein without undue experimentation.

As will be discussed in further detail below with reference to FIG. 4, the stress indicator 120 provides the physician 130 with an indication regarding whether the shear applied to the therapeutic cells 110 is within an acceptable level. In various exemplary embodiments, the stress indicator 120 can provide visual information or some appropriate cue or feedback that the physician 130 can perceive via eyesight. The visual information can be provided as color, a gauge or a meter, a digital display, or a graphical user interface ("GUI"), to name some examples without producing an exhaustive list. In certain exemplary embodiments, the stress indicator 120 can provide audible information, so that the physician 130 can receive feedback or an appropriate cue that the physician 130 can hear. Audible information can include a tone, a pitch that may change according to shear level, a spoken warning, or a bell, to mention some representative options. In certain exemplary embodiments, the stress indicator 120 provides a cue or feedback that the physician 130 can feel, for example via a hand or finger. Stress information can be communicated haptically, via sense of touch, tactilely, via vibration, or via force feedback. Force feedback can include providing resistance against the force that the physician 130 is applying to the plunger 105 of the syringe 175. The plunger 105 can exert additional resistance to the physician's depression force if the level of shear is exceeding (or is approaching) a level that may result in a diminished level of effectiveness of the therapeutic cells 110.

Figure 3:
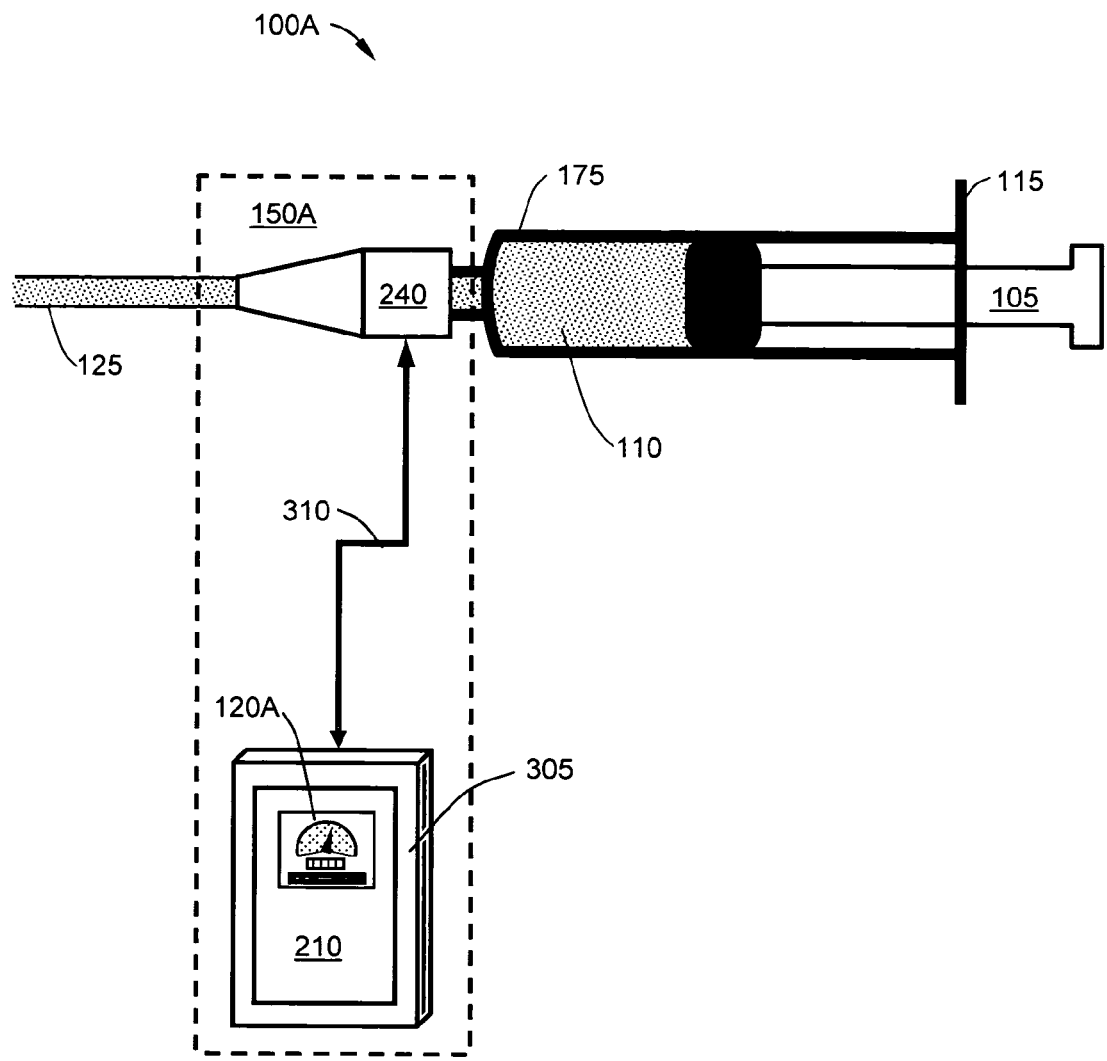
FIG. 3 is an illustration of a system for delivering a therapeutic agent comprising an apparatus for monitoring stress in accordance with certain exemplary embodiments of the present invention.

Turning now to FIG. 3, this figure illustrates an exemplary system 100A for delivering a therapeutic agent 110 comprising an apparatus 150A for monitoring stress according to certain embodiments of the present invention. As discussed above, certain exemplary embodiments of the therapeutic agent 110 comprises progenitor cells, stem cells, regenerative cells, cells delivered for regenerative medicine, cells having an ability to differentiate, or cells that secrete or cause the production of a substance that provides therapeutic benefit. Accordingly, the therapeutic agent 110 of FIG. 3 will be discussed as the therapeutic cells 110, without implying that the embodiment of FIG. 3 is limited in application to stem cells or progenitor cells. Similarly, the apparatus 150A for monitoring stress of FIG. 3 will be discussed in a non-limiting manner as the shear monitor 150A.

In the exemplary embodiment of FIG. 3, the shear monitor 15A comprises a handheld computing system 305 that comprises the computing engine 210, the stress indicator 120A, and the database 230, which are discussed above with reference to FIG. 2. The flow meter 240 is attached to the catheter 125 and the syringe 175. The flow meter 240 measures (or otherwise characterizes) the flow rate of the therapeutic cells 110 exiting the syringe 175 and entering the catheter 125 for delivery into the patient 140 as discussed above.

The flow meter 240 outputs a signal carrying flow rate information to the handheld computing system 305 via the signal line 310. The signal line 310 is typically a flexible wire that conducts electrical or electromagnetic signals. That is, the signal line 310 can comprise two or more individually insulated electrical conductors. In certain embodiments, the signal line 310 can comprise a waveguide, an optical fiber, a metallic conductor, or some other appropriate signal transmission medium. In certain exemplary embodiments, the signal line 310 can be a wireless link, so that the handheld computing system 305 and the flow meter 240 communicate via transmitting signals in open air, for example via radio waves, via radio frequency ("RF") communications, via electromagnetic waves or radiation, or via light propagating in open air.

In certain exemplary embodiments, the physician 130 inputs the dosage 220 and the catheter identification 215 manually, via a user interface of the handheld computing system 305. Such a user interface can be a GUI associated with the stress indicator 120A, a touch screen, a keypad, a microphone with an associated speech recognition capability, or some other appropriate facility for providing input.

Figure 4:
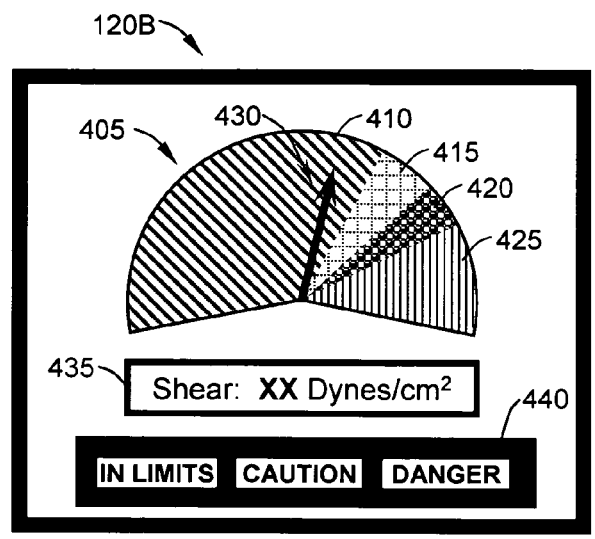
FIG. 4 is an illustration of a display of a system for monitoring stress associated with delivering a therapeutic agent in accordance with certain exemplary embodiments of the present invention.

Turning now to FIG. 4, this figure illustrates an exemplary display 120B of a system 150/150A for monitoring stress associated with delivering a therapeutic agent 110 according to certain embodiments of the present invention. The display 120B illustrated in FIG. 4 provides an exemplary embodiment of the stress indicator 120A illustrated in FIG. 3 and thus will be described with exemplary reference to FIG. 3 and preceding figures as appropriate. In various exemplary embodiments, the display 120B can comprise a computer monitor, a GUI, a flat panel display, a backlit display, a cathode ray tube ("CRT"), a liquid crystal display, a touch screen, a plasma display, a display of a cell phone, a display of a handheld, an electronic display, an electronically driven display, a light emitter, an arrangement of light emitting diodes ("LEDs"), a display of a personal organizer, etc.

As illustrated, the display 120B includes a digitally generated graphic 405 emulating a traditional swinging needle meter, typically of common automobile speedometers in cars. The graphic 405 includes four colored zones 410, 415, 420, 425. The zone 410 is green to indicate that stress/shear is within a range that is believed to be acceptable. The zone 415 is yellow to indicate that stress/shear is at a level that warrants caution. The zone 420 is orange to indicate that stress/shear is approaching a level that may negatively impact effectiveness or that otherwise warrants elevated caution. The zone 425 is red to indicate that stress/shear has exceeded acceptable limits and that effectiveness of the therapeutic cells 110 is being compromised. The digitally generated needle 420 of the graphic 405 swings to the appropriate zone 410, 415, 425, 425 based on the shear computed by the shear module 250 as compared to thresholds and/or criteria, as discussed below with reference to FIG. 8.

In certain exemplary embodiments, the graphic 405 indicates peak shear, which as discussed above may vary from the average shear as a result of shear variations occurring during heart beats. Alternatively, the graphic 405 indicates average shear, based on a moving average, or as averaged over each heart beat, for example.

In addition to the graphic 405, the exemplary display 120B comprises an alphanumeric area 435 that displays shear level in units of dynes per square centimeter (or some other appropriate units). As discussed above, the graphic 405 can alternatively display some other measure or indication of stress, such as temperature (for example in degrees Centigrade, Celsius, Kelvin, or Fahrenheit); pressure (for example in pounds per square inch or Newtons per square meter); acceleration (for example in meters per second per second); oxidative stress; time until the therapeutic cells 110 may suffer from ischemia, lack of oxygen, or lack of appropriate nutrients; or other factor relevant to maintain viability or effectiveness of the therapeutic cells 110. The values displayed in the alphanumeric area 435 can be peak stress, average stress, accumulated stress, or a moving average. Further the values can be derived via various statistical techniques and data processing routines available in the data processing, statistics, and DSP arts.

The exemplary display 120B also comprises a graphical area 440 providing a status. The graphical area 440 can flash "IN LIMITS," "CAUTION," or "DANGER" according to whether the shear being applied to the therapeutic cells 110 is within limits believed acceptable, at a level that warrants caution, or beyond a threshold that may impact effectiveness, respectively. As discussed above, shear information may also (or alternatively) be communicated to the physician 130 via sound or in a manner that the physician 130 (or some other operator) can feel, via a hand or other appendage for example.

Figure 5:
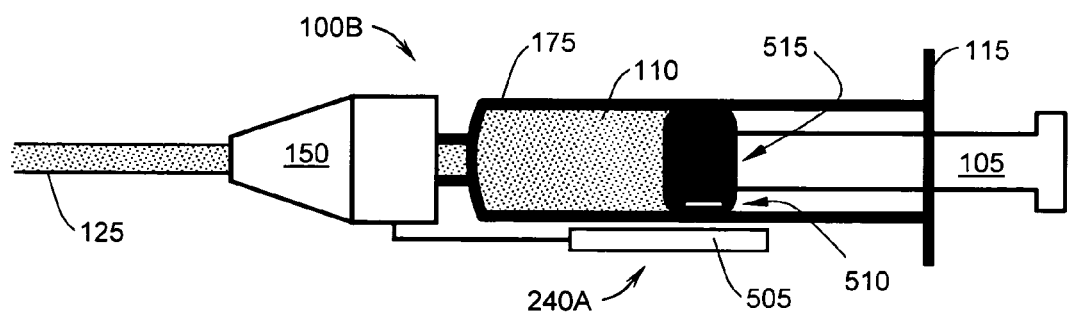
FIG. 5 is an illustration of a system for delivering a therapeutic agent comprising an apparatus for monitoring stress in accordance with certain exemplary embodiments of the present invention.

Turning now to FIG. 5, this figure illustrates an exemplary system 100B for delivering a therapeutic agent 110 comprising an apparatus 150 for monitoring stress according to certain embodiments of the present invention. As discussed above, certain exemplary embodiments of the therapeutic agent 110 comprise progenitor cells, stem cells, therapeutic cell, or cells having an ability to differentiate (note that these descriptions of cells are not necessarily mutually exclusive with respect to one another). Accordingly, the therapeutic agent 110 of FIG. 5 can be referred to as the therapeutic cells 110 in the context of one example out of others supported by the present teachings and disclosure. Similarly, the apparatus 150 for monitoring stress of FIG. 5 can be referred to in a non-limiting manner as the shear monitor 150, as discussed above.

The system 100B comprises a flow meter 240A for monitoring flow of the therapeutic cells 110 into the catheter 125. In this instance, the flow meter 240A comprises a detector array 505 that responds to a target 510 embedded in the sealing end 515 of the syringe's plunger 105. In an exemplary embodiment, the detector array 505 comprises multiple magnetic sensing elements or metal detecting elements. The target 510 comprises a magnet, a piece of ferromagnetic material, or iron to which the detector array 505 is responsive. The detector array 505 determines the location of the target 510, and thus the extent to which the plunger 105 has been depressed, according to which element or elements of the detector array 505 have detected the target 510. Taking a mathematical derivative with respect to time of the position of the target 510 yields delivery rate or flow rate of the therapeutic cells 110. In other words, the rate of change in the position of the target 510, as determined by the detector array 505, correlates with flow rate of the therapeutic cells 110.

Accordingly, the flow meter 240A can monitor the rate of cell delivery and/or the rate of flow of the therapeutic cells 110 through the system 110B, including through the catheter 125. The output of the flow meter 240A can be used as an alternative to the output of the flow meter embodiments discussed above. Or, the flow meter 240A and the flow meter 240, discussed above, can operate in parallel with one another. That is, certain exemplary embodiments can include both the flow meter 240 and the flow meter 240A.

Figure 6:
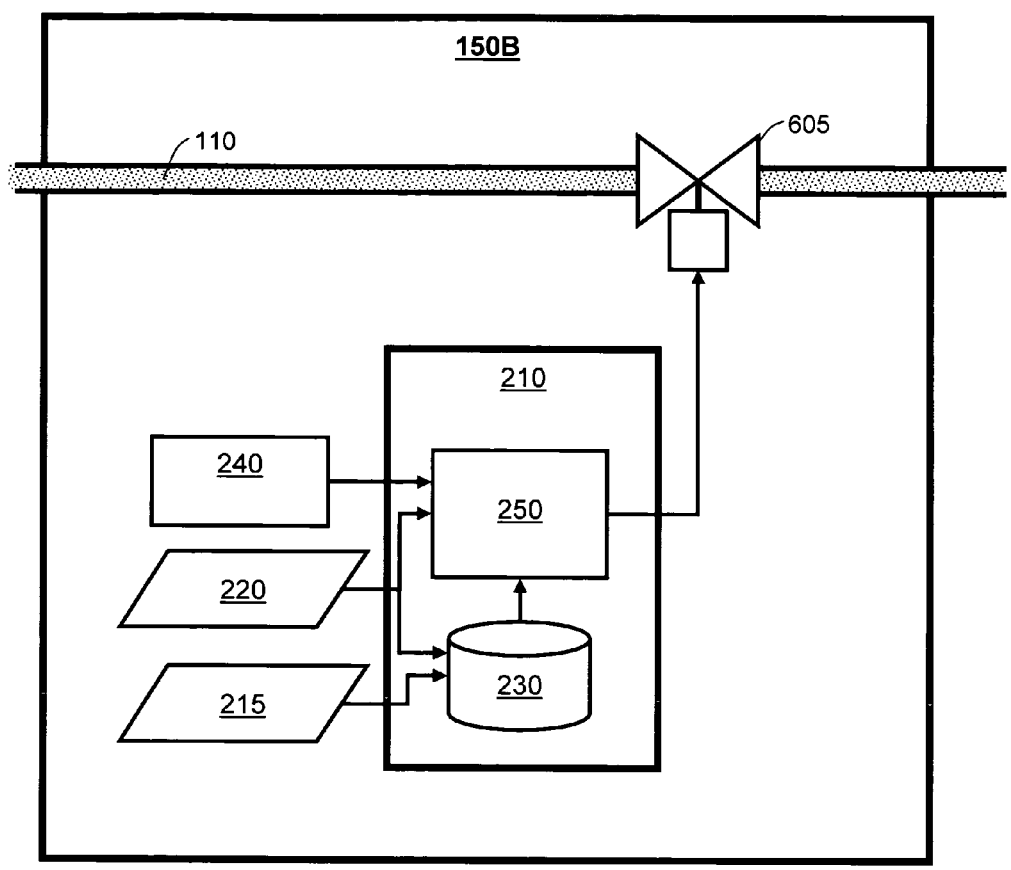
FIG. 6 is a functional block diagram of a system for monitoring and controlling stress applied to a therapeutic agent in connection with delivery in accordance with certain exemplary embodiments of the present invention.

Turning now to FIG. 6, this figure illustrates an exemplary functional block diagram of a system 150B for monitoring and controlling stress applied to a therapeutic agent 110 in connection with delivery according to certain embodiments of the present invention. As discussed above, in certain exemplary embodiments, the therapeutic agent 110 can comprise various types of cells appropriate for delivery in a treatment context, including cells that change or differentiate to provide a cellular form suited for treatment and/or cells that intended to help regenerate tissue or to promote organ regeneration. Accordingly, the therapeutic agent 110 illustrated in FIG. 6 can be referred to as the therapeutic cells 110.

In an exemplary embodiment, the system 150B is connected between the syringe 175 and the catheter 125 to regulate flow between the syringe 175 and the catheter 125. Regulating the flow in this manner helps keep the physician 130 from implementing a flow rate that would reduce the effectiveness of the therapeutic cells 110.

The computing engine 210 in the system 150B of FIG. 6 provides a capability for automatically controlling or regulating stress on the therapeutic cells 110 in connection with delivery. When shear approaches a level that risks impairing effectiveness of the therapeutic cells 110, the computing engine 210 prompts the valve 605 to close (at least partially), thereby reducing shear. In other words, the computing engine 210 controls the valve 605 to adjust the flow rate of the therapeutic cells 110, thereby maintaining flow rate within acceptable limits and avoiding a decrease in therapeutic effectiveness. Alternatively, the valve 605 can be automatically manipulated to control pressure, wherein excessive pressure or pressure change can impair certain therapeutic agents.

Turning now to FIG. 7, this figure illustrates a schematic of an exemplary apparatus that reads information from a component of a therapeutic agent delivery system according to certain embodiments of the present invention. More specifically, FIG. 7 illustrates an exemplary shear monitor 150C that comprises a barcode reader 750 for reading a barcode 725 attached to a catheter 125. The barcode reader 750 thereby identifies the catheter 125 and provides the catheter identification 215 to the computing engine 210. As discussed above with reference to FIG. 2, the computing engine 210 references the catheter identification 215 to the catheter database 230 to obtain catheter parameters relevant to computing shear (or some other form of stress) on the therapeutic cells 110.

As an alternative to a barcode 725 and a barcode reader 750, the shear monitor 150C can comprise a radio frequency identification ("RFID") scheme. In such a system, an RFID tag is attached to or otherwise associated with the catheter 125. The shear monitor 150 comprises an RFID reader that automatically identifies the catheter 125 based on the RFID tag.

As another alternative to barcode-based identification, the catheter 125 can comprise magnetic marks or a pattern of magnetic material encoded with information that the shear monitor 150C reads via a magnetic code reader.

In the embodiment of FIG. 7, the barcode reader 750 is integrated into the shear monitor's housing. Alternatively, the barcode reader 750 can be a commercial unit as commonly available. The barcode 725 can be attached directly to the catheter 125 or attached to packaging of the catheter 125. In operation, the physician 130 places the barcode 725 in the commercially available barcode reader unit. The unit identifies the catheter 125 and then transmits the identification to the shear monitor's computing engine 210, for example over a copper wire or via wireless communication. Thus, in certain exemplary embodiments, the shear monitor 150C can comprise multiple units in multiple housings that communicate with one another via wired, fiber optic, or wireless communication.

Similarly, identification based on RFD) technology can be either implemented within a unitary housing that is attached to the syringe (as illustrated in FIG. 1A) or as multiple devices that are individually housed and that communicate with one another via one or more wires, optical fibers, or wireless/RF communication links. Such devices may even be located on different tables or in different equipment locations within a room.

Turning now to FIG. 8, this figure illustrates a flowchart of an exemplary process 800 for delivering a therapeutic agent 110 while monitoring stress on the therapeutic agent 110 according to certain embodiments of the present invention. Process 800, which is entitled "Monitor Stress," will be discussed with exemplary reference to certain elements shown in FIGS. 1-7 and discussed above. Those with ordinary skill in the art having benefit of this disclosure will appreciate that such reference provides but one example, that process 800 is one example out of many others supported by this teaching, and that the present disclosure describes and teaches a wide range of processes and methods for making and using exemplary embodiments of the present invention.

Exemplary embodiments of process 800, as well as various other processes and process steps described herein can involve computer programming and/or computer-implemented steps. That is, one or more computer programs can carry out certain steps and functions described herein and illustrated in flowchart form. However, it should be apparent that there could be many different ways of implementing the present invention, via computer programming and otherwise. The present invention should not be construed as limited to any one set of computer program instructions. Further, a skilled programmer would be able to write a computer program to implement appropriate aspects of the disclosed technology without difficulty based on the flow charts and associated description in the application text, for example. Therefore, disclosure of a particular set of program code instructions is not considered necessary for an adequate understanding of how to make and use the present invention. The functionality of certain computer-implemented embodiments will be explained in more detail in the following description in conjunction with FIG. 8 illustrating an exemplary process flow.

Certain steps in process 800, as well as the other methods and processes disclosed and taught herein, must naturally precede others for the present invention to function as described. However, the present invention is not limited to the order of the steps described if such order or sequence does not adversely alter the functionality of the present invention. That is, it is recognized that some steps may be performed before or after other steps or in parallel with other steps without departing from the scope and spirit of the present invention.

At step 805 of process 800, the physician 130 determines an appropriate type and amount of the therapeutic cells 110 for treatment and loads the therapeutic cells 110 into the barrel or chamber of the syringe 175. In many cases, the therapeutic cells 110 will be extracted from the patient 140 and processed in advance of executing process 800. The physician 130 enters the dosage 220 into the computing engine 210 as discussed above. Often, the dosage 220 will include a volume fraction. That is, the therapeutic cells 110 can be delivered in a carrier fluid, for example as a suspension. The ratio of cells-to-carrier-fluid and the viscosity of the fluid and/or the resulting composition may be specified or computed in connection with determining and monitoring shear and stress.

At step 810, the computing engine 210 receives the catheter identification 215. The physician 130 typically selects an appropriate catheter 125, based on professional judgment, and perhaps with consideration to personal preference. The physician 130 may enter the catheter identification 215 manually or scan a label or tag associated with the catheter 125 with a reader. Alternatively, the computing engine 210 automatically detects the catheter identification 215, for example via an integral code reader 750 that automatically reads a barcode 725 (or some other code) attached to the catheter 125.

The shear module 250 queries the database 230 with the catheter identification 215. In response to the query, the database 230 provides geometrical and physical parameters of the specific catheter 125 selected by the physician 130. As discussed above, the database 230 contains a list of catheters (for example organized via model number and manufacturer) tabulated with the parameters of each catheter 125 that are relevant to computing shear or some other form of stress. Accordingly, the shear module 250 retrieves appropriate catheter parameters from the database 230.

At step 815, the shear module 250 retrieves from the database 230 shear sensitivity for the specific therapeutic cells 110 and dosage 220 prescribed by the physician 130 and/or ranges of shear that the therapeutic cells 110 and dosage 220 can tolerate. As discussed above, the database 230 contains a lookup table of the shear/stress sensitivities of various therapeutic cells 110 and dosages 220. Accordingly, the shear module 250 sets shear ranges based on shear sensitivity information retrieved from the database 230.

The sensitivity data can be obtained empirically, via laboratory testing of various therapeutic cell types and various other therapeutic agents, or based on experience. In one exemplary embodiment, shear is monitored and archived; therapeutic outcomes are tracked; correlations are made between shear and therapeutic outcome (Did the patient's condition improve?); and the database 230 is updated accordingly. Thus, the database 230 can evolve and improve over time.

At step 820, the physician 130 inserts the catheter 125 into the patient 140. As discussed above, the physician 130 may position the catheter 125 for delivery of the therapeutic cells 110 to a diseased or damaged area of the patient's cardiovascular system, a wound, peripheral vascular system, an area of the lungs, brain tissue, a bladder, etc. In some situations, such as in wound care, the physician 130 may position the catheter manually. In other cases, the physician 130 may utilize imaging technology, for example in connection with delivering the therapeutic cells 110 to cardiac tissue. The physician 130, may also deliver therapeutic cells through a channel of an endoscope that carries optical images from the tissue site to an eyepiece or to a display.

At step 825, input from the physician 130 triggers or causes the therapeutic cells 110 to move out of the syringe 175 and into the patient 140, often into or onto a specific area selected for treatment. In an exemplary embodiment, the physician 130 squeezes the syringe 175 as discussed above. Alternatively, the physician 130 may engage an electrically powered pump or some other appropriate electrical device which urges the therapeutic cells 110 through and out of the catheter 125. Thus, the delivery can be fully manual or implemented with a machine under control of the physician 130 (or operated by some other person participating in the procedure).

At step 827, a shear monitoring loop initiates iteration of steps 830 through 890 as discussed below. The loop begins at step 827 and ends at step 893.

At step 830, the flow meter 240 monitors flow rate of the therapeutic cells 110 in the catheter 825. Monitoring flow rate typically proceeds as discussed in detail above. The flow meter 240 can comprise any of a wide range of devices and systems that evaluate flow and/or movement of material through the catheter 825, either directly or indirectly. In one exemplary embodiment, a single pressure sensor tracks pressure applied to the therapeutic cells 110 during the procedure.

As step 835, the shear module 250 receives flow information from the flow meter 240. The shear module 250 computes shear on the therapeutic cells 110 based on the monitored flow, the dosage 220, and catheter parameters accessed at step 810 of process 800. In an exemplary embodiment, the shear computations proceed as discussed above in detail.

At step 840, the shear module 250 compares the computed shear to the stress ranges obtained at step 815 of process 800. Steps 845, 850, and 855 describe exemplary logic associated with the comparison.

Figure 8B:
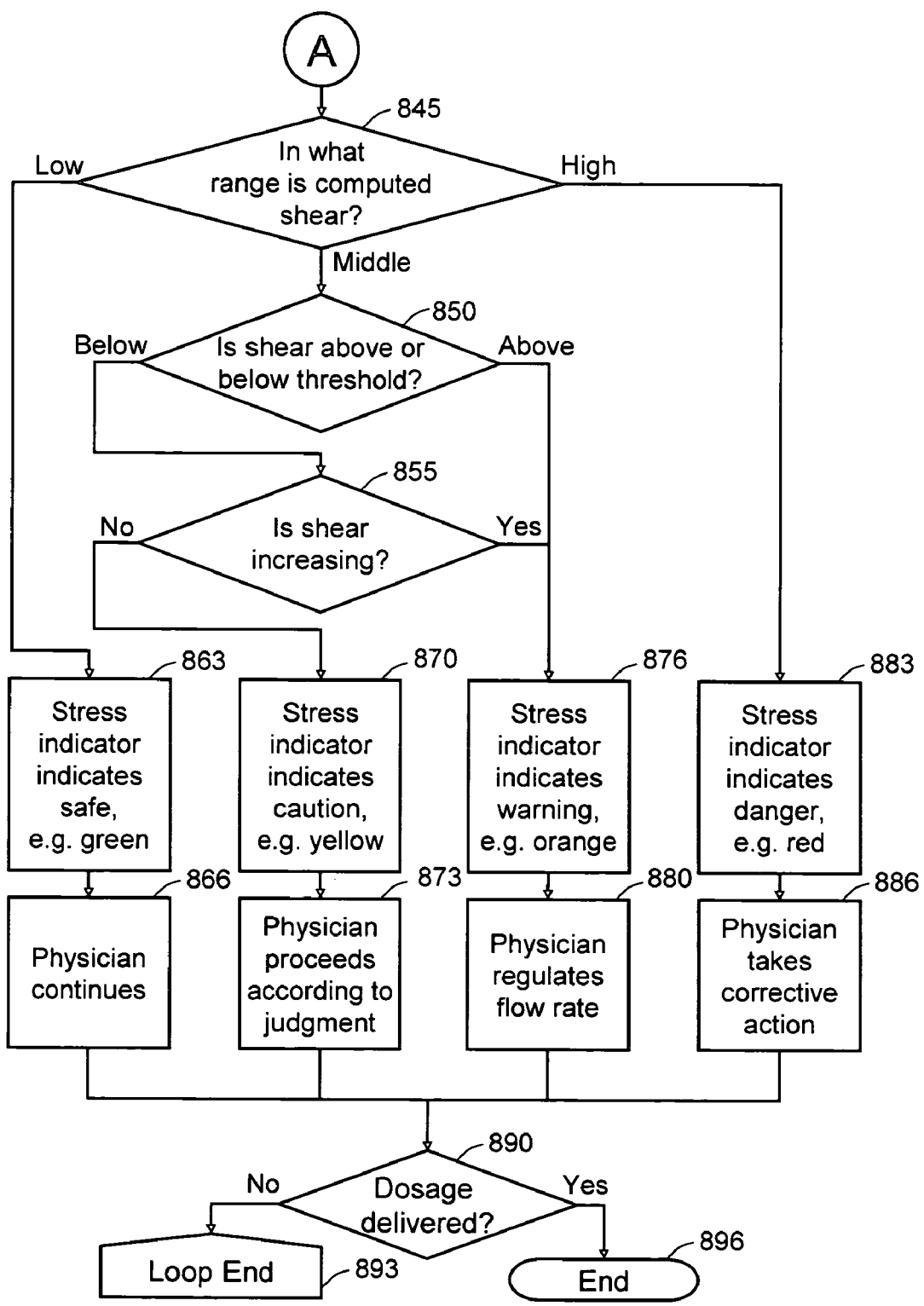

At inquiry step 845, represented in FIG. 8B, the shear module 250 determines whether the computed shear is within one of three ranges (three being a representative rather than restrictive number of ranges). If shear is within the lowest of the three ranges, steps 863 and 866 follow execution of step 845.

At step 863, the display 120B of the stress indicator 120/120A indicates that stress is at a level believed to be safe. As discussed above, criteria for determining safety or risk can be set according to laboratory tests on the therapeutic cells 110, for example via evaluating the amount of a protein (or other substance) produced at various levels of stress and/or shear, wherein the amount is correlated with risk or a change in therapeutic efficacy. That is, the therapeutic cells 110 may emit or produce a particular biochemical or provide particular assay results that vary with the amount of shear applied. The high and low criteria of step 845 and the threshold of step 850 can be set based on such levels. Moreover, such criteria and threshold can be refined based on experience. As the database 230 expands from tracking therapeutic outcomes for various levels of shear and/or stress conditions over many patients 140, criteria and thresholds for advising a physician 130 can be refined or implemented with finer levels of detail.

Displaying a green status, as discussed above with reference to FIG. 4, is one example of providing the physician 130 with the information in a format suited for visual reception. Thus, the graphic 405 can display the needle 430 in the green zone 405. The graphic 405 can further present status information in the graphical area 440 as discussed above. Further, the display 120B can display shear as a number in the alphanumeric area 435. At step 866, the physician 130 monitors the stress indicator 120/120A, determines that shear is being managed appropriately, and continues delivering the therapeutic cells 110.

If the shear module 250 determines at step 845 that the computed shear is within the high range, then process 800 proceeds to steps 883 and 886 from step 845. At step 883, the stress indicator 120/120B indicates that stress is at a level that may reduce effectiveness of the therapeutic cells 110 (or otherwise lead to some unwanted or unexpected therapeutic outcome). In an exemplary embodiment, to warn the physician 130, the needle 430 appears in the red zone 425, the alphanumeric area 435 shows a high shear value, and the graphic area 440 presents the text "DANGER." As discussed above, the stress indicator 120/120B can emit sound for hearing, vibration for feeling, or some other form of energy that the physician 130 can usefully perceive. At step 886, the physician 130 takes corrective action in response to the indication provided by the stress indicator 120/120B, for example releasing pressure on the syringe 175 or adjusting a control knob of an electrically driven machine that moves the therapeutic cells 110. Thus, the physician 130 uses the shear monitor 150 as feedback for maintaining shear within an appropriate level.

If the shear module 250 determines at step 845 that shear is within a middle range, then process 800 proceeds down a third processing branch, beginning with execution of inquiry step 850. At step 850, the shear module 250 determines whether the computed shear is above or below a threshold level within the middle range of shear values.

If the computed shear is below the threshold, then inquiry step 855 determines whether the shear is increasing. If shear is not increasing then, steps 870 and 873 execute. Thus, step 870 executes if shear is within a predetermined range and is either stable or decreasing. At step 870, the stress indicator 120/120A provides an appropriate status indication. As discussed above with reference to FIG. 4, in an exemplary embodiment, the display 120B places the needle 430 in the yellow zone 415, shows the computed shear values in the alphanumeric area 435, and may present a cautionary message in the graphic area 440. At step 873, the physician 130 proceeds according to medical judgment, which may include monitoring the situation or decreasing the flow rate of the therapeutic cells 110. For example, the physician 130 may elect to increase the flow rate if judgment dictates that the cell-delivery procedure should be expedited.

If the shear module 250 determines at step 850 that shear is above the threshold then steps 876 and 880 execute. Steps 876 and 880 also execute if shear is below the threshold and increasing, as determined respectively at steps 850 and 855. Thus, a trend of increasing shear may warrant an elevated level of caution, even if the shear has not yet reached a critical level.

As step 876, the stress indicator 120/120B issues a warning. Issuing the warning can comprise swinging the needle 430 into the orange zone 415, displaying shear numbers in the alphanumeric area 435, presenting appropriate text in the graphic area 440, and/or issuing sound, vibration, force feedback, etc. perceptible by the physician 130. Step 876 provides an exemplary embodiment of issuing an alert, a notification, or a message for receipt or perception by the physician 130; likewise, each of steps 863, 870, and 883 provides such an exemplary embodiment. At step 880, the physician regulates the flow rate so as to avoid unacceptably reducing effectiveness of the therapeutic cells 110.

As discussed above with reference to FIG. 6, the computing engine 210 can also (or alternatively) take corrective action automatically. That is, steps 866, 873, 880, and 866 can comprise automatic control that augments or replaces intervention of the physician 130. Such automatic control can comprise moving the valve 605, switching electricity, interrupting an action of the physician 130, or engaging an appropriate actuator, for example.

Following execution of step 866, step 873, step 880, or step 866 (depending on how process 800 branched), inquiry step 890 determines whether delivery of the dosage 220 is complete. In an exemplary embodiment, the physician 130 determines whether the therapeutic cells 110 have exited the syringe 175, typically via the physician 130 fully depressing the plunger 105. If delivery is complete, then process 800 ends at step 896. Otherwise, loop end step 893 directs execution back to the loop start step 827, whereby process 800 proceeds with execution of step 830 as discussed above. Thus, process 800 iterates monitoring shear and providing the physician 130 with delivery guidance, via executing steps 830 through 890 as appropriate, until the full dosage 220 of therapeutic cells 110 have been delivered, at which point process 800 ends with the execution of step 896 as discussed above.

Technology for monitoring delivery of a therapeutic agent has been described in detail so as to enable one of ordinary skill in the art to make and use the technology without undue experimentation. From the description, it will be appreciated that an embodiment of the present invention overcomes limitations of the prior art. Those skilled in the art will appreciate that the present invention is not limited to any specifically discussed application or implementation and that the embodiments described herein are illustrative and not restrictive. From the description of the exemplary embodiments, equivalents of the elements shown herein will suggest themselves to those skilled in the art, and ways of constructing other embodiments of the present invention will appear to ordinary practitioners of the art. Therefore, the scope of the present invention is to be limited only by the accompanying claims.

What is claimed is:

1. A method for conducting cell-based therapy, comprising the steps of:
   monitoring movement of the stem or progenitor cells through a catheter at least partially disposed in a vascular lumen of a patient, when a person is controlling a medical procedure;
   measuring a level of stress on the stem or progenitor cells associated with the movement;
   supporting regulation of the movement of the stem or progenitor cells in response to the measured level of stress on the stem or progenitor cells by providing an indication of the measured level of stress to the person; and providing a control for the level of stress on the stem or progenitor cells by looping the steps of measuring the level of stress and supporting regulation of the movement.

2. The method of claim 1, wherein providing the indication comprises providing information to the person in support of the person regulating flow of the stem or progenitor cells through the catheter.

3. The method of claim 1, wherein providing the indication comprises presenting information on a display.

4. The method of claim 1, wherein providing the indication comprises providing audible or tactile feedback to the person.

5. The method of claim 1, wherein measuring the level of stress comprises evaluating whether the movement of the stem or progenitor cells is reducing effectiveness of the stem or progenitor cells.

6. The method of claim 1, wherein measuring the level of stress comprises monitoring the movement of the stem or progenitor cells during the medical procedure with a flow meter.

7. The method of claim 1, wherein measuring a level of stress comprises monitoring shear stress on the stem or progenitor cells occurring during movement of the stem or progenitor cells through the catheter at least partially disposed in the vascular lumen of the patient.

8. The method of claim 7, further comprising the step of archiving the monitored shear stress in a database that tracks therapeutic outcomes.

9. The method of claim 1, wherein providing the indication comprises displaying the measured level of stress on an electronic display comprising a graphical area that advises the person whether the measured level of stress is in each of a plurality of predefined ranges.

10. The method of claim 1, wherein the step of measuring the level of stress comprises determining peak shear based on shear variation occurring during a heart beat, and wherein providing the indication comprises presenting peak shear data on a display that is electrically powered.

11. A method for conducting cell-based therapy, comprising the steps of:

monitoring movement of therapeutic cells through a catheter, wherein the movement is controlled in association a medical procedure;

measuring a level of stress on the therapeutic cells associated with the monitored movement;

determining a shear on the therapeutic cells based on the measured level of stress;

providing an indication of the shear to support regulation of the movement of the therapeutic cells through the catheter in response to the determined shear on the therapeutic cells; and establishing control for the shear on the therapeutic cells by the supported regulation of the movement of the therapeutic cells through the catheter.

12. The method of claim 11, wherein the catheter is sized for delivering the therapeutic cells to a beating heart, and wherein determining shear comprises determining flow measurements associated with the beating heart.

13. The method of claim 11, wherein determining shear on the therapeutic cells comprises determining shear based on a volume fraction and a viscosity associated with the therapeutic cells.

14. The method of claim 11, wherein monitoring movement comprises sampling an output from a flow meter.

15. The method of claim 11, wherein monitoring movement comprises sampling an output from a flow meter comprising:

a target disposed in a sealing end of a plunger of a syringe; and a detector array disposed adjacent a barrel of the syringe and operable to determine positions of the target, and wherein the method comprises determining flow measurements by computing mathematical derivatives of the positions with respect to time.

16. A method for conducting cell-based therapy, comprising the steps of:

monitoring movement of therapeutic cells through a catheter, wherein the movement is controlled in association the cell-based therapy;

determining a shear on the therapeutic cells based on the monitored movement of the therapeutic cells;

providing an indication of the shear to support regulation of the movement of the therapeutic cells through the catheter in response to the determined shear on the therapeutic cells; and establishing control for the shear on the therapeutic cells by repeatedly supported regulation of the movement of the therapeutic cells through the catheter as part of the cell-based therapy.

17. The method of claim 16, further comprising:

comparing the determined shear to a plurality of thresholds;

selecting a message associated with the respective one of the plurality of thresholds; and displaying the selected message on an electronically driven display for receipt by a healthcare practitioner participating in the cell-based therapy.

18. The method of claim 16, further comprising:

comparing the determined shear at the selected time during the beating cycle of a heart to a plurality of the thresholds;

selecting a message associated with the respective one of the plurality of thresholds; and displaying the selected message on an electronically driven display for receipt by a healthcare practitioner participating in the cell-based therapy.

19. The method of claim 16, further comprising the step of presenting the determined shear on an electronically driven display using a graphic that comprises differently colored zones for indicating level of the determined shear.

20. The method of claim 16, where providing an indication comprises sounding an audible alarm or providing a back-pressure on the catheter configured to provide a tactile feedback to a healthcare practitioner participating in the cell-based therapy.

* * * * *